US00PP32634P2

(12) United States Plant Patent
Bernuetz

(10) Patent No.: US PP32,634 P2
(45) Date of Patent: Dec. 15, 2020

(54) ***EUPHORBIA* PLANT NAMED 'BONPRI 14105'**

(50) Latin Name: *Euphorbia pulcherrima Willd. ex Klotzsch X Euphorbia cornastra*
Varietal Denomination: Bonpri 14105

(71) Applicant: Andrew Bernuetz, Silverdale (AU)

(72) Inventor: Andrew Bernuetz, Silverdale (AU)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 0 days.

(21) Appl. No.: 16/873,398

(22) Filed: Apr. 4, 2020

(51) Int. Cl.
*A01H 5/02* (2018.01)
*A01H 6/38* (2018.01)

(52) U.S. Cl.
USPC ..... Plt./306

(58) Field of Classification Search
USPC ..... Plt./263.1, 302, 303, 306
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Euphorbia* plant named 'Bonpri 14105', characterized by its upright and mounded plant habit; vigorous growth habit; freely branching habit; inflorescences with light pink and light yellow green-colored flower bracts; relatively small cyathia; and good post-production longevity.

1 Drawing Sheet

Figure 1:
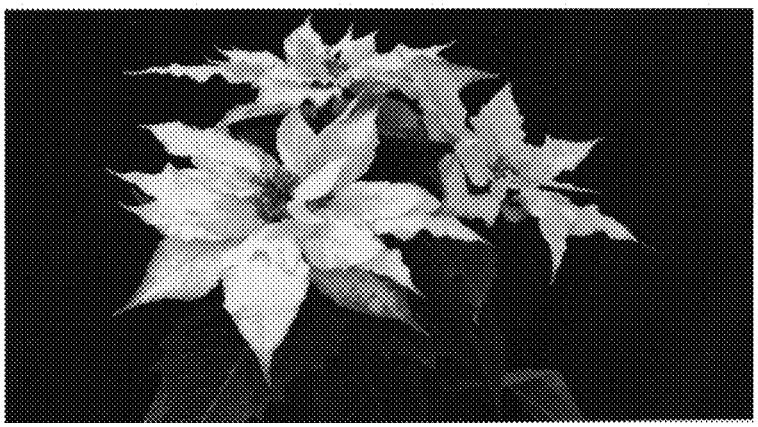

Botanical designation: *Euphorbia pulcherrima* Willd. ex Klotzsch X *Euphorbia cornastra.*

Cultivar denomination: 'BONPRI 14105'.

BACKGROUND OF THE INVENTION

The present invention relates to a new and distinct cultivar of *Euphorbia* plant, an interspecific hybrid botanically known as *Euphorbia pulcherrima* Willd. ex Klotzsch X *Euphorbia cornastra*, and hereinafter referred to by the cultivar name 'Bonpri 14105'.

The new *Euphorbia* plant is a product of a planned breeding program conducted by the Inventor in Yellow Rock, New South Wales, Australia. The objective of the program is to create and develop new interspecific *Euphorbia* plants with compact, upright and mounded plant habit and attractive flower bracts.

The new *Euphorbia* plant is a naturally-occurring whole plant mutation of a proprietary selection of *Euphorbia pulcherrima* Willd. ex Klotzsch X *Euphorbia cornastra* identified as code number 1080, not patented. The new *Euphorbia* plant was discovered and selected by the Inventor as a single flowering plant from within a population of plants of the mutation parent selection in a controlled greenhouse environment in Yellow Rock, New South Wales, Australia on Oct. 24, 2014.

Asexual reproduction of the new *Euphorbia* plant by terminal vegetative cuttings in a controlled greenhouse environment in Yellow Rock, New South Wales, Australia since October, 2014 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bonpri 14105'. These characteristics in combination distinguish 'Bonpri 14105' as a new and distinct *Euphorbia* plant:

1. Upright and mounded plant habit.
2. Vigorous growth habit.
3. Freely branching habit.
4. Inflorescences with light pink and light yellow green-colored flower bracts.
5. Relatively small cyathia.
6. Good post-production longevity.

Plants of the new *Euphorbia* differ primarily from plants of the mutation parent selection in flower bract color as flower bracts of plants of the new *Euphorbia* are light pink and light yellow green in color whereas flower bracts of plants of the mutation parent selection are pink in color.

Plants of the new *Euphorbia* can be compared to plants of the *Euphorbia pulcherrima* Willd. ex Klotzsch X *Euphorbia cornastra* 'Bonpri 515', disclosed in U.S. Plant Pat. No. 25,587. In side-by-side comparisons, plants of the new *Euphorbia* differ primarily from plants of 'Bonpri 515' in flower 1. Plants of the new *Euphorbia* have smaller leaves than plants of 'Bonpri 515'.
2. Plants of the new *Euphorbia* flower about 20 days later than plants of 'Bonpri 515'.
3. Inflorescences of plants of the new *Euphorbia* have fewer and smaller flower bracts than inflorescences of plants of 'Bonpri 515'.
4. Plants of the new *Euphorbia* and 'Bonpri 515' differ in flower bract color as flower bracts of plants of the new

*Euphorbia* are light pink and light yellow green in color whereas flower bracts of plants of 'Bonpri 515' are bright red purple in color.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the top of the sheet (FIG. 1 of 2) is a side perspective view of a typical flowering plant of 'Bonpri 14105' grown in a container.

Figure 2:
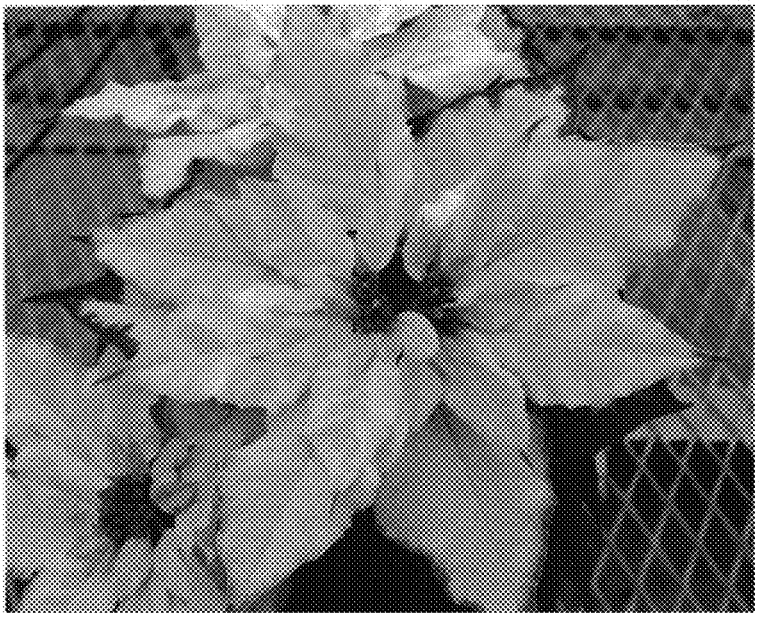

The photograph at the bottom of the sheet (FIG. 2 of 2) is a top perspective close-up view of a typical flowering plant of 'Bonpri 14105'.

DETAILED BOTANICAL DESCRIPTION

Plants used in the aforementioned photographs and described herewith in detail were grown during the autumn and early winter in 12-cm containers in an outdoor nursery in Higashiomi, Shiga, Japan and under cultural practices typical of commercial *Euphorbia* production. During the production of the plants, day temperatures averaged 23° C. and night temperatures averaged 13° C. Plants were six months old when the photographs and the description were taken. In the following description, color references are made to The Royal Horticultural Society Colour Chart, 2015 Edition, except where general terms of ordinary dictionary significance are used.

Botanical classification: *Euphorbia pulcherrima* Willd. ex Klotzsch X *Euphorbia cornastra* 'Bonpri 14105'.

Parentage: Naturally-occurring whole plant mutation of a proprietary selection of *Euphorbia pulcherrima* Willd. ex Klotzsch X *Euphorbia cornastra* identified as code number 1080, not patented.

Propagation:

*Type*.—Terminal vegetative cuttings.

*Time to initiate roots, summer*.—About seven days at temperatures about 20° C. to 25° C.

*Time to initiate roots, winter*.—About nine days at temperatures about 20° C. to 22° C.

*Time to produce a rooted young plant, summer*.—About three weeks at temperatures about 20° C. to 25° C.

*Time to produce a rooted young plant, winter*.—About four weeks at temperatures about 20° C. to 22° C.

*Root description*.—Fibrous; typically white in color, actual color of the roots is dependent on substrate composition, water quality, fertilizers, substrate temperature and physiological age of roots.

*Rooting habit*.—Freely branching; medium density.

Plant description:

*Plant habit and form*.—Upright and mounded plant habit; inverted triangle; inflorescences positioned above the foliar plane; vigorous growth habit.

*Plant height*.—About 23.6 cm.

*Plant diameter or spread*.—About 30 cm.

*Lateral branch description*.—Branching habit: Freely branching habit, about four lateral branches develop per plant. Length: About 13 cm. Diameter: About 5.3 mm. Internode length: About 2.5 cm. Aspect: Mostly upright to somewhat outward. Strength: Strong. Texture: Smooth, glabrous. Color: Close to 137C.

*Leaf description*.—Arrangement: Alternate, simple. Length: About 8.2 cm. Width: About 5.4 cm. Shape: Ovate with moderately shallow lobes. Apex: Acute. Base: Rounded. Margin: Serrate; undulate. Venation pattern: Pinnate, reticulate. Texture and luster, upper and lower surfaces: Smooth, glabrous; rough; matte. Color: Developing leaves, upper surface: Close to 143A. Developing leaves, lower surface: Close to 143B. Fully developed leaves, upper surface: Close to 137A and N144A; venation, close to 143B. Fully developed leaves, lower surface: Close to 137B; venation, close to 145D. Petioles: Length: About 2.3 cm. Diameter: About 2.1 mm. Texture, upper and lower surfaces: Sparsely pubescent. Color, upper and lower surfaces: Close to 143B.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—One per lateral branch, about four inflorescences develop per plant.

*Inflorescence diameter*.—About 17.9 cm.

*Inflorescence height*.—About 5.5 cm.

*Fragrance*.—None detected.

*Natural flowering season*.—Plants typically flower during the autumn and winter in Japan; inflorescence initiation and development can also be induced under artificial long nyctoperiod and short photoperiod conditions; late flowering response, plants flower about 70 days under natural season or photoinductive conditions in Japan.

*Post-production longevity*.—Good post-production longevity; plants of the new *Euphorbia* maintain good substance and bract color for about seven weeks.

*Flower bracts*.—Quantity per inflorescence: About 22. Length: About 4.5 cm. Width: About 2 cm. Shape: Elliptic. Apex: Acute. Base: Obtuse. Margin: Serrate; undulate. Texture, upper and lower surfaces: Smooth, glabrous. Aspect: Upright to outwardly. Venation pattern: Pinnate, reticulate. Color: Transitional bracts, upper and lower surfaces: Close to 73D, 65C and 157D; towards the margins, close to 143B. Developing bracts, upper and lower surfaces: Close to 73C; towards the margins, close to 144D. Fully expanded bracts, upper surface: Close to 65A and 149D; towards the margins, close to 143B; venation, close to 149D. Fully expanded bracts, lower surface: Close to 65A and 149D; towards the margins, close to 143B; venation, close to 196D. Flower bract petioles: Length: About 6 mm. Diameter: About 1.8 mm. Texture, upper and lower surfaces: Smooth, glabrous. Color, upper and lower surfaces: Close to 145D.

*Cyathia*.—Quantity per corymb: About 24. Diameter of cyathia cluster: About 2.5 cm. Height, individual cyathium: About 4.4 mm. Diameter, individual cyathium: About 5.4 mm. Shape, individual cyathium: Globose. Color: Towards the apex, close to 4C; mid-section and base, close to 144C. Nectaries:

Quantity per cyathium: One. Size: About 1.6 mm by 2.8 mm. Texture: Smooth, glabrous. Color: Close to 9B.

*Peduncles*.—Length: About 2.5 mm. Diameter: About 1.7 mm. Texture, upper and lower surfaces: Smooth, glabrous. Aspect: Mostly upright. Color, upper and lower surfaces: Close to 144C.

*Reproductive organs*.—None observed on plants of the new *Euphorbia*.

*Seeds and fruits*.—To date, seed and fruit production has not been observed on plants of the new *Euphorbia*.

Pathogen & pest resistance: Plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'Bonpri 14105' as illustrated and described.

* * * * *